United States Patent [19]

Ernst et al.

[11] Patent Number: 4,518,813

[45] Date of Patent: May 21, 1985

[54] OPTICALLY ACTIVE UNITS FOR THE SYNTHESIS OF THE SIDE CHAIN OF (R,R,R)-α-TOCOPHEROL AND THEIR PREPARATION

[75] Inventors: Hansgeorg Ernst, Ludwigshafen; Friedrich Vogel, Wachenheim; Joachim Paust, Neuhofen, all of Fed. Rep. of Germany

[73] Assignee: BASF Aktiengesellschaft, Ludwigshafen, Fed. Rep. of Germany

[21] Appl. No.: 430,695

[22] Filed: Sep. 30, 1982

[30] Foreign Application Priority Data

Oct. 2, 1981 [DE] Fed. Rep. of Germany ....... 3139238

[51] Int. Cl.$^3$ ................. C07C 17/16; C07C 17/26; C07C 19/02
[52] U.S. Cl. .................. 570/241; 562/602; 568/841; 568/878; 570/101; 570/181; 570/252; 570/257; 570/261
[58] Field of Search ............... 562/602; 570/181, 252, 570/261, 253, 241, 257, 101; 568/841, 878

[56] References Cited

U.S. PATENT DOCUMENTS

4,000,174 12/1976 Henrick et al. ............... 560/122
4,026,907 5/1977 Scott et al. .................... 549/407
4,206,156 6/1980 Kamiya et al. ................ 424/211

FOREIGN PATENT DOCUMENTS

1812268 6/1970 Fed. Rep. of Germany .
2455017 11/1980 France .
2488888 2/1982 France .
48-3804 2/1973 Japan .
788349 12/1957 United Kingdom .

OTHER PUBLICATIONS

*J. Org. Chem.*, vol. 41, No. 22, (1976), pp. 3505-3511, 3512-3515, Cohen et al.
*J. Org. Chem.*, vol. 43, No. 18, (1978), pp. 3435-3440, Chan et al.
*Beilsteins Handbuch der Organischen Chemie*, Suppl. IV, vol. 2, p. 860, (1975).
*Chemical Abstracts*, vol. 58, Abstract No. 6946b, (1963), Price, J. A., "Polymers of 3,7-dimethyl-1-octene and 4,6,6-trimethyl-1-heptene".
*Chemical Abstracts*, vol. 65, Abstract No. 3727a, (1966), Mukerji et al., "Investigation of the Offensive Odor of Hemiptera Bugs".
*Chemical Abstracts*, vol. 86, p. 385, abstract No. 16214j, (1977), Som et al., "Rotational Isomerism in 1--bromo-3-chloro-2-methylpropane".
*Chemical Abstracts*, vol. 91, p. 613, Abstract No. 174752r, (1979), Takahashi et al., "An Alternative Synthesis of (2R,6R)-(-)-2,6,10-trimethylundecyl bromide, The Key Intermediate in the Synthesis of Natural α-Tocopherol".
*J. American Chem. Soc.*, vol. 78, No. 6, pp. 1193-1198, (1956), Eliel et al., "The Mechanism of Halide Reductions with Lithium Aluminum Hydride".
*J. Organometallic Chem.*, vol. 122, pp. 123-128, (1976), Le Borgne, "Etude Des Aldimines Lithiees".

Eleil, E. "Stereochemistry of Carbon Compounds", McGraw-Hill Book Co., Inc., New York (1962), pp. 47-65.
Houben-Weyl, "Methoden Der Organ. Chemie", vol. 412, (1955), pp. 519-522 and 530.
Jacques et al., "Enantiomers, Racemates and Resolutions", John Wiley and Sons, New York, (1981), pp. 253-259.

*Primary Examiner*—Natalie Trousof
*Assistant Examiner*—Patricia M. Scott
*Attorney, Agent, or Firm*—Oblon, Fisher Spivak, McClelland and Maier

[57] ABSTRACT

(2R,6R)-1-Chloro-2,6,10-trimethyl-undecane I, (R)-(+)-β-chloro-isobutyric acid II, (S)-(+)-1-bromo-3-chloro-2-methylpropane IV and (2R)-(+)-1-chloro-2,6-dimethyl-heptane V are novel optically active units for the synthesis of the side chain of (R,R,R)-α-tocopherol. In the process according to the invention, the optically active C$_{14}$-chloride I is obtained in 6 simple reaction steps starting from II, via the novel intermediates IV and V, in accordance with the following equation:

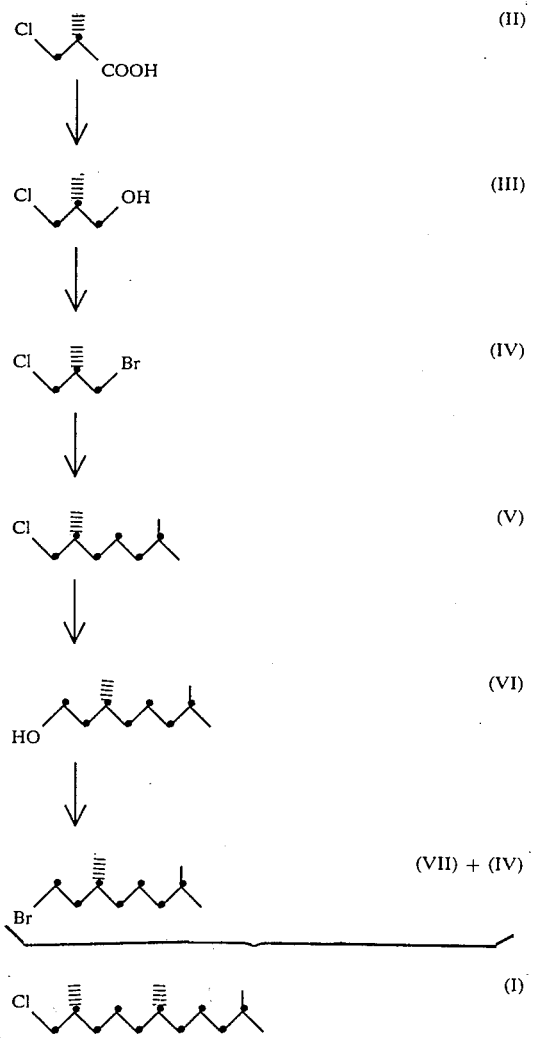

4 Claims, No Drawings

OPTICALLY ACTIVE UNITS FOR THE SYNTHESIS OF THE SIDE CHAIN OF (R,R,R)-α-TOCOPHEROL AND THEIR PREPARATION

The present invention relates to (2R,6R)-1-chloro-2,6,10-trimethyl)-undecane (I), (R)-(+)-β-chloro-isobutyric acid (II), (S)-(+)-1-bromo-3-chloro-2-methyl-propane (IV) and (2R)-(+)-1-chloro-2,6-dimethyl-heptane (V), a process for the preparation of I starting from II, via the novel compounds IV and V, and the use of the novel compounds I, II, IV and V as optically active units for the synthesis of the side chain of natural optically active vitamin E, ie. (2R,4′R,8′R)-α-tocopherol of the formula

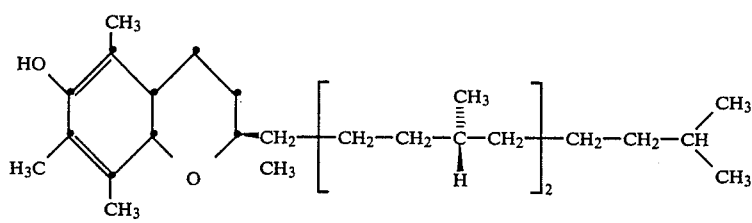

The substituents in the above optically active structural formula and in the other optically active structural formulae used in this application which are in front of the plane of the molecule are indicated by ▮, and those behind the plane of the molecule are indicated by ⦀. Substituents of structural formulae which are not drawn in stereochemical form can be in either the R or the S orientation, or the compound can be in the form of a mixture of the R- and S-isomers.

J. Org. Chem. 41 (1976), 3505 et seq. and German Laid-Open Application DOS No. 2,602,507 disclose that natural vitamin E can be prepared by means of a Wittig reaction of a chroman-2-carboxaldehyde of the formula VIII

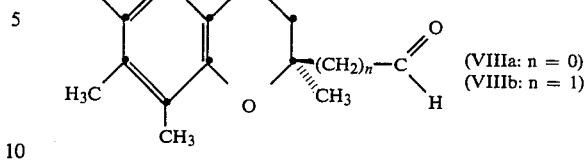

and the corresponding optically active $C_{15}$- or $C_{14}$-side chain intermediate. The side chain of natural vitamin E has 2 centers of asymmetry, both of which are in the R-configuration. Processes are known for the preparation of an optically active side chain intermediate having 14 C atoms, in which the starting materials are optically active units having a lower carbon number and the two centers of asymmetry are produced by using such a chiral unit twice (cf. loc.cit.). In principle, these processes start from (S)-(+)-3-hydroxy-2-methyl-propanoic acid, which is converted into the optically active $C_4$-unit (S)-(+)-3-tert.-butoxy-2-methyl-1-bromo-propane XIII in the manner outlined in scheme 1, via etherification/esterification with boron trifluoride/isobutylene to give X, alanate reduction to give XI and bromination. XIII is extended by one $C_1$-unit by reaction with NaCN to give the nitrile XIV and subsequent reduction of the nitrile to give the aldehyde XV, or by nitrile hydrolysis to give the acid XX, reduction thereof to the carbinol XXI and subsequent tosylation to give the tosylate XXII.

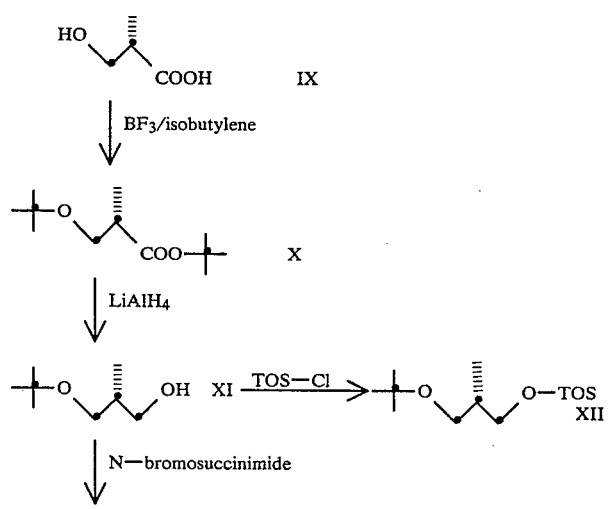

4,518,813
-continued
Scheme 1
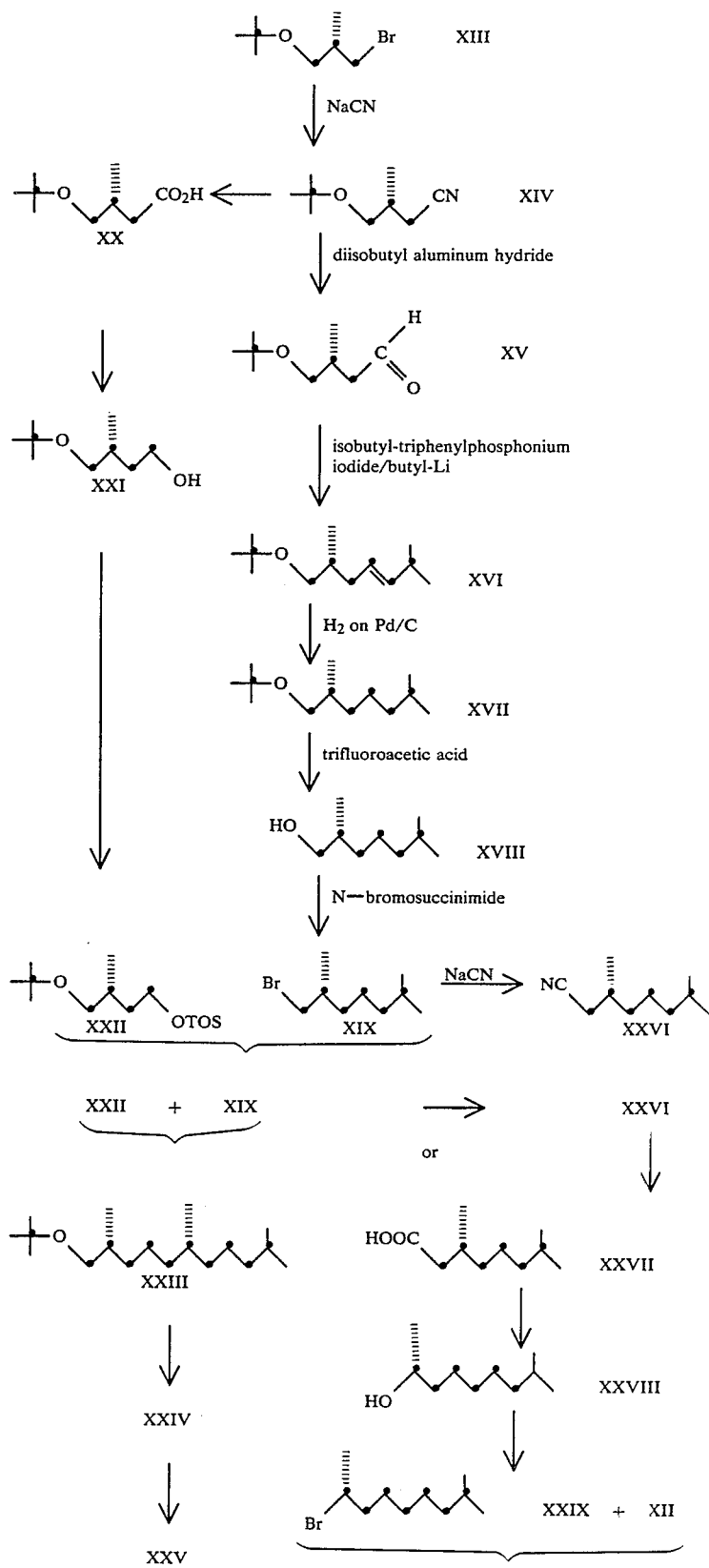

Scheme 1

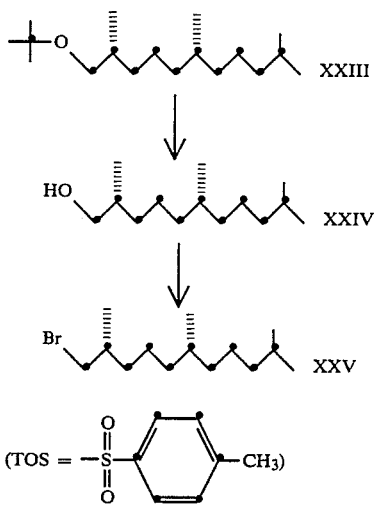

(TOS = tosyl group shown)

The C$_9$-bromide XIX is prepared from the aldehyde XV by a Wittig reaction with isobutyl-triphenylphosphonium iodide, hydrogenation, butyl ether cleavage and bromination, and the bromide is coupled to the tosylate XXII to give the C$_{14}$-ether, which, after ether cleavage, can be brominated to give the C$_{14}$-bromide XXV.

Alternatively, the C$_1$-unit is introduced with cyanide at the stage of the C$_9$-bromide XIX. The nitrile XXVI is converted into the C$_{10}$-bromide XXIX by hydrolysis, reduction and bromination, and the bromide can then be coupled with the tosylate XII prepared from XI to give the C$_{14}$-ether XXIII.

The disadvantages of this process are, on the one hand, that, as yet, the (S)-(+)-3-hydroxy-2-methyl-propanoic acid required as the starting compound can be prepared only by bacterial oxidation of isobutyric acid, and such microbiological processes are technically quite complicated and expensive, or can be obtained in only a very poor yield by resolution of the racemate (cf. Biochem. Z. 342 (1965), 256 and 265), and, on the other hand, that from 15 to 17 reaction stages are necessary for preparation of the optically active C$_{14}$-bromide XXV, depending on the variant.

It is an object of the present invention to provide a technically less complicated synthesis route to an optically active C$_{14}$-side chain intermediate which can be reacted with chroman-2-carboxaldehyde of the formula VIII to give (2R,4'R,6R')-α-tocopherol.

We have found that this object is achieved with (2R)-(+)-β-chloro-isobutyric acid II, which is a relatively easily accessible optically active starting compound from which the novel optically active C$_{14}$-unit (2R,6R)-1-chloro-2,6,10-trimethylundecane I can be obtained in only 6 reaction stages via the novel optically active intermediate (2S)-(+)-1-bromo-3-chloro-2-methyl-propane IV and (2R)-(+)-1-chloro-2,6-dimethyl-heptane V.

The present invention relates to the novel optically active intermediates I, II, IV and V and their use as optically active units for the synthesis of the side chain of (R,R,R)-α-tocopherol, and to a process for the preparation of the C$_{14}$-unit (2R,6R)-1-chloro-2,6,10-trimethyl-undecane of the formula I

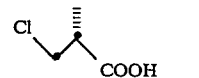

wherein (A) the novel (R)-(+)-β-chloro-isobutyric acid of the formula II

is used as the optically active starting material, (B) this starting material is reduced with boron hydride, boron hydride derivatives or lithium aluminum hydride,. preferably with boron hydride or boron hydride derivatives, to give (R)-(−)-3-chloro-2-methyl-propanol of the formula III

(C) this compound is brominated with phosphorus tribromide, with triphenylphosphine and bromine in dimethylformamide, or with triphenylphosphine and carbon tetrabromide in methylene chloride to give the novel (S)-(+)-1-bromo-3-chloro-2-methyl-propane of the formula IV

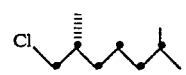

(D) this compound is converted into the novel (2R)-(+)-1-chloro-2,6-dimethylheptane of the formula V with isopentyl-magnesium bromide in an inert ethereal solvent in the presence of a di-alkali metal tetrahalocuprate, preferably dilithium tetrachlorocuprate, (E) the product in D is converted into (3R)-3,7-dimethyloctan-1-ol of the formula VI

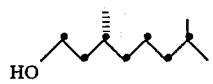

(VI)

by treatment with metallic magnesium and subsequent introduction of gaseous formaldehyde, (F) the product in E is brominated by a method similar to that in C to give (3R)-1-bromo-3,7-dimethyloctane of the formula VII

(VII)

and (G) this compound is converted, by treatment with metallic magnesium, into the corresponding Grignard compound, which can be reacted with (S)-(+)-1-bromo-3-chloro-2-methylpropane in an ethereal solvent in the presence of a dialkali metal tetrahalocuprate, preferably dilithium tetrachlorocuprate, to give I.

The novel process to obtain the $C_{14}$-unit I has the following substantial advantages compared with the conventional processes for the preparation of optically active $C_{14}$-side chain intermediates:

(1) An optically active starting material which is technically more readily accessible is used.

(2) From 15 to 17 reaction steps, depending on the variant, are necessary for carrying out the known processes starting from the optically active starting material IX to obtain the $C_{14}$-bromide XXV, while the $C_{14}$-chloride I is obtained from the optically active starting material II in only 6 reaction steps in the novel process.

(3) Using halides as intermediates eliminates the necessity of providing hydroxyl groups with expensive protective groups such as the tert.-butyl group or the tosylate group, and of subsequently converting the ether group into a halide in several stages.

(4) The use of formaldehyde as the $C_1$-unit means a substantial shortening of the synthesis route compared with the long and complicated sequence of cyanide formation, hydrolysis, reduction and halogenation.

(5) With regard to the technical realization of the novel process, it is particularly advantageous that the same reaction steps, such as bromination or Grignard reaction, is repeated several times.

(2R)-(+)-β-Chloro-isobutyric acid II is used as the optically active starting material in the process according to the invention, and can be prepared by resolution of racemic β-chloro-isobutyric acid, which is known and can be obtained by adduct formation of methacrylic acid with HCl (cf. C.A. 68 (1968) 21 900 n).

According to our most recent results, racemic β-chloro-isobutyric acid can be prepared substantially more advantageously if, instead of gassing an ethereal solution of methacrylic acid with HCl at 0° C. (loc.cit.), the methacrylic acid is reacted at from 100° to 160° C. in an autoclave with concentrated aqueous hydrochloric acid under the autogenous pressure (not more than about 15 bar), or with HCl gas which has been forced in (not more than about 40 bar). Solutions of from 10 to 40 percent by weight of methacrylic acid in conventional concentrated hydrochloric acid are generally used in the reaction with aqueous hydrochloric acid. This improvement to the process reduces the reaction time from about 40 hours to from 1 to 2 hours, giving about the same yield.

Resolution of the racemate is advantageously effected by repeated recrystallization of the mixture of the diastereomeric salts of the racemic acid with d-ephedrine from an organic solvent, such as ethyl acetate or toluene, subsequent splitting of the salts by dissolving in dilute acid, such as HCl or $H_2SO_4$, and extraction with a suitable organic solvent.

The mixture of the diastereomeric salts is obtained by adding a solution of d-ephedrine in an organic solvent, eg. diethyl ether, diisopropyl ether, methyl tert.-butyl ether, acetone, methyl ethyl ketone, toluene or ethyl acetate, to a solution of the racemic acid in a corresponding solvent.

Last but not least, the principle of obtaining the required optically active $C_4$-unit via resolution of racemic β-chloro-isobutyric acid is advantageous since the S-(−)-isomer which cannot be used is racemized in a simple manner by heating with concentrated aqueous hydrochloric acid or HCl gas in an autoclave at from 100° to 160° C., and thus can be used again for resolution of the racemate.

The optically active acid II can be reduced to the alcohol III with boron hydride or a boron hydride derivative, such as a $BH_3$-tetrahydrofuran complex, a $BH_3$-dimethylsulfide complex, gaseous diborane or a combination of $NaBH_4$ and $BF_3$, or with lithium aluminum hydride, in a solvent, eg. diethyl ether, tetrahydrofuran or diethylene glycol dimethyl ether (diglyme). Reduction with boron hydride or a boron hydride derivative is particularly advantageous since it proceeds very rapidly, even under mild conditions, and working up of the reaction mixture is substantially simpler (no precipitation of a voluminous precipitate) than when lithium aluminum hydride is used.

From 0.3 to 1.5 moles of hydride per mole of II is generally used, and the reduction is generally carried out at not more than 50° C. over a period of from 1 to 6 hours.

Reduction of β-chloro-isobutyric acid to 3-chloro-2-methyl-propanol has not yet been described in the literature. Only reduction of β-chloro-carboxylic acids, eg. 3-chloro-3-methyl-butyric acid and 3-chloro-butyric acid, with lithium aluminum hydride has been disclosed (cf. J. Am. Chem. Soc. 78 (1956), 4049), but this gives only unsatisfactory yields since a substantial amount of the acid is dehalogenated during the reaction.

The reduction of 11-bromo-undecanecarboxylic acid with a borane-dimethylsulfide complex to give 11-bromo-undecanol has also been disclosed (cf. Aldrichimica Acta 8 (1975) 20), as has the reduction of purely aliphatic carboxylic acids or α-halocarboxylic acids (chloroacetic acid) with a borane-tetrahydrofuran complex (cf. J. Org. Chem. 38 (1973) 2786 et seq.).

Optically active 3-chloro-2-methyl-propanol has recently been disclosed in French Pat. No. 79 10 589 (Publication No. 2,455,017) and French Pat. No. 79 10 050 (No. 2,454,465), according to which it is prepared by stereospecific hydrolysis of an alkyl ester by means of pancreas lipase on a carrier material.

Bromination of the alcohol III to give the novel (S)-(+)-1-bromo-3-chloro-2-methyl-propane IV is advantageously effected with phosphorus tribromide, with a triphenyl phosphine/bromine mixture in dimethylformamide, or with a triphenylphosphine/carbon tetrabromide mixture in methylene chloride. However, it can also be carried out with HBr in the form of a gas or concentrated aqueous solution.

From 0.3 to 2, preferably from 0.5 to 1.5, moles of brominating agent are generaly used per mole of III, and the bromination is carried out at from 0° to 100° C., preferably from 25° to 90° C., over a period of from about 1 to 6 hours.

The reaction of the dihalide IV with isopentylmagnesium bromide in an inert ethereal solvent in the presence of a catalytic amount of a di-alkali metal tetrahalocuprate surprisingly leads to the chloride V with completely selective replacement of the bromine. Examples of inert ethereal solvents for this reaction are dioxane, diethyl ether, diethylene glycol dimethyl ether and dimethoxyethane, but preferably tetrahydrofuran. Dilithium tetrachlorocuprate is preferably used as the dialkali metal tetrahalocuprate. The 1-chloro-2,6-dimethylheptane obtained in this reaction has hitherto also only been disclosed as a racemate (cf. Bioorg. Chem. 7 (1978) 235 et seq., especially 245).

The chloride V is dissolved in an ethereal solvent, preferably in diethyl ether or tetrahydrofuran, and this solution is treated with about the equimolar amount of metallic magnesium in an ethereal solvent. The reaction mixture is refluxed for from one to several hours and cooled and gaseous formaldehyde, which can be obtained by, for example, heating dry paraformaldehyde to 180° C., is passed in until, in accordance with the method of H. Gilman (J. Amer. Chem. Soc. 47 (1925) 2002) the Grignard reagent can no longer be detected in the reaction mixture. From about 1 to 1.5 moles of formaldehyde are taken up, and the reaction takes from about 30 to 60 minutes.

The (3R)-3,7-dimethyl-octan-1-ol VI thereby obtained can be isolated from the reaction mixture in a conventional manner, for example by adding ice and dilute sulfuric acid and then subjecting the mixture to steam distillation. The aqueous phase of the distillate is extracted with an ether and the combined organic phases are dried and distilled.

The bromination of the alcohol VI to give (3R)-1-bromo-3,7-dimethyl-octane VII is advantageously carried out by one of the bromination methods described above.

The $C_{10}$-bromide VII is converted into the corresponding Grignard compound by treatment with metallic magnesium in an ethereal solvent, and the Grignard compound is then coupled with (S)-(+)-1-bromo-3-chloro-2-methylpropane IV in the presence of a catalytic amount of a dialkali metal tetrahalocuprate, preferably di-lithium tetrachlorocuprate, to give (2R,6R)-1-chloro-2,6,10-trimethyl-undecane I.

With the aid of the process according to the invention, it is possible to obtain the novel compound (2R,6R)-1-chloro-2,6,10-trimethyl-undecane I starting from the novel, readily accessible optically active starting material (2R)-(+)-β-chloro-isobutyric acid in only 6 simple reaction steps via novel optically active intermediates. I is an important intermediate for the synthesis of (R,R,R)-α-tocopherol.

EXAMPLE 1

Preparation of (R)-(+)-β-chloro-isobutyric acid (a) Preparation of racemic β-chloro-isobutyric acid 1.3 kg of methacrylic acid are stirred with 10 l of concentrated aqueous hydrochloric acid at 110° C. in an autoclave for 1 hour. The reaction mixture is then cooled and extracted with methylene chloride, the extract is washed with water, dried over magnesium sulfate and concentrated and, finally, the residue is distilled at 108° C./20 mm Hg to give 1.69 kg of β-chloro-isobutyric acid, which, according to analysis by gas chromatography (GC) is 98% pure. This corresponds to a yield of 91% of theory.

(b) (R)-(+)-β-Chloro-isobutyric acid (II) from racemic β-chloro-isobutyric acid 300 g (1.82 moles) of d-ephedrine in 1,600 ml of diisopropyl ether are added at room temperature to 500 g (4.08 moles) of (+)-β-chloro-isobutyric acid in 400 ml of diisopropyl ether. The mixtue is refluxed for 1 hour, stirred at room temperature for 2 hours and filtered with suction at 15° C. 478 g (92%) of the d-ephedrine salt are obtained.

The salt is recrystallized ten times from ethyl acetate, until its optical rotation remains constant. 35.0 g of d-ephedrine salt of melting point 124°–126° C. are obtained.

$[\alpha]_D^{25} = +30.47°$ (C=5.106/CH$_3$OH)

The ephedrine salt is dissolved in 2N hydrochloric acid, the solution is extracted with ether, the extract is washed with 2N hydrochloric acid, dried over sodium sulfate and concentrated and the residue is then distilled to give 13.1 g of II of boiling point 107° C./16 mm Hg.

$[\alpha]_D^{25} = 12.73°$ (C=5.854/CH$_3$OH)

EXAMPLE 2

(R)-(−)-3-Chloro-2-methyl-propanol (II)

12.3 g (0.1 mole) of (R)-(+)-β-chloro-isobutyric acid are added dropwise to a suspension of 3.8 g (0.1 mole) of sodium borohydride in 100 ml of tetrahydrofuran at room temperature in the course of 1 hour. The mixture is stirred at room temperature for 30 minutes and a solution of 17 g (0.12 mole) of boron trifluoride etherate in 20 ml of tetrahydrofuran is then added dropwise in the course of 1 hour, during which the reaction mixture is kept at room temperature. The mixture is stirred at room temperature for 2 hours and is then poured onto ice and extracted with ether, and the extract is washed acid-free with sodium bicarbonate, dried and concentrated.

The residue is purified by distillation to give 7.8 g of III of boiling point 77° C./28 mm Hg, corresponding to a yield of 72% of theory.

$[\alpha]_D^{25} = -13.0°$ (C=4.82/CH$_3$OH)

EXAMPLE 3

(S)-(+)-1-Bromo-3-chloro-2-methyl-propane (IV)

54.2 g (0.2 mole) of phosphorus tribromide are added to 46.7 g of (R)-(+)-3-chloro-2-methyl-propanol (according to GC, 97% pure=0.418 mole) at from 0° to 10° C. in the course of 30 minutes. The reaction mixture is then stirred at 90° C. for 5 hours and then poured onto ice and extracted with petroleum ether and the extract is washed with bicarbonate solution, dried over sodium sulfate and concentrated.

The residue is purified by distillation to give 53.4 g of IV of boiling point 53° C./24 mm Hg, corresponding to a yield of 74% of theory.

$[\alpha]_D^{25} = 0.36°$ (C=5.043/CH$_3$OH)

EXAMPLE 4

(2R)-(+)-1-Chloro-2,6-dimethylheptane V 135 g (0.89 mole) of 1-bromo-3-methylbutane in 300 ml of tetrahydrofuran are added dropwise to 22 g (0.905 mole) of magnesium in 100 ml of tetrahydrofuran. The mixture is stirred at 40° C. for 1½ hours and then, at −15° C., 63.6 g (0.37 mole) of (S)-(+)-1-bromo-3-chloro-2-methylpropane in 50 ml of tetrahydrofuran are added dropwise, followed by 34.8 ml of a 0.5M solution of dilithium tetrachlorocuprate in tetrahydrofuran. The mixture is stirred at −15° C. for 3 hours and is left to stand at room temperature overnight. It is acidified with about 30 ml of 30% strength sulfuric acid and then subjected to steam distillation. The organic phase of the distillate is separated off and the aqueous phase is extracted with ether. The combined organic phases are dried over sodium sulfate and concentrated to give 74.5 g of residue which, according to GC, contains 65% of V, corresponding to a yield of 80.5% of theory.

The residue is purified by distillation to give 44.4 g of V of boiling point 72° C./16 mm Hg (74% of theory).

$[\alpha]_D^{25} = +2.15$ (C=2.925/CH$_3$OH)

EXAMPLE 5

(3R)-3,7-Dimethyloctan-1-ol (VI)

9.92 g of (2R-(+)-1-chloro-2,6-dimethylheptane in 35 ml of tetrahydrofuran are added to 2 g of magnesium in 10 ml of tetrahydrofuran. The mixture is refluxed for 2½ hours and gaseous formaldehyde, which is produced by heating 3.5 g of dry paraformaldehyde to 180° C., is then passed in at room temperature.

10 g of ice and 6 ml of 30% strength sulfuric acid are added to the reaction mixture, and the mixture is subjected to steam distillation. The aqueous phase of the distillate is extracted twice with ether and the combined organic phases are dried over sodium sulfate and concentrated to give 8.56 g of residue which, according to GC, contains 91% of VI, corresponding to a yield of 81% of theory.

The residue is purified by distillation to give 6.7 g (=70% of theory) of VI of boiling point 80° C./6 mm Hg $[\alpha]_D^{25} = 4.9°$ (pure)

EXAMPLE 6

(3R)-1-Bromo-3,7-dimethyloctane (VII)

5.77 g (0.022 mole) of phosphorus tribromide are added dropwise to 7.6 g (0.048 mole) of (R)-3,7-dimethyloctan-1-ol at from 5° to 10° C. The mixture is then stirred at 100° C. for 6 hours, cooled, poured onto ice and extracted with petroleum ether and the extract is washed with bicarbonate solution, dried over sodium sulfate and concentrated to give 11.3 g of residue which, according to GC, contains 81.4% of the bromide VII, corresponding to a yield of 87% of theory.

The residue is purified by distillation to give 7.9 g of VII of boiling point 84° C./8 mm Hg (75% of theory)

$[\alpha]_D^{25} = -5.93°$ (pure)

EXAMPLE 7

(2R,6R)-1-Chloro-2,6,10-trimethyl-undecane (I)

16.4 g (0.074 mole) of (3R)-1-bromo-3,7-dimethyloctane are added dropwise to 2.0 g (0.082 mole) of magnesium in 50 ml of tetrahydrofuran. The mixture is stirred at 40° C. for 1½ hours and then cooled to −15° C. At this temperature, 7.42 g (0.043 mole) of (S)-(+)-1-bromo-3-chloro-2-methyl-propane are added, followed by 2.1 ml of a 0.5M solution of di-lithium tetrachlorocuprate in tetrahydrofuran. The mixture is stirred at −15° C. for 2 hours and is then allowed to reach room temperature. 15 ml of saturated ammonium chloride solution are added, the mixture is extracted with ether and the extract is dried over sodium sulfate and concentrated.

7.4 g of I of boiling point 72°–75° C./0.1 mm Hg are obtained, corresponding to a yield of 74% of theory.

$[\alpha]_D^{25} = +2.2°$ (C=1.890/CHCl$_3$)

We claim:

1. A process for the preparation of (2R,6R)-1-chloro-2,6,10-trimethylundecane of the formula

which comprises:

(a) reducing (R)-(+)-β-chloroisobutyric acid of the formula II

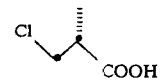

with a boron hydride reducing agent or lithium aluminum hydride to give (R)-(−)-3-chloro-2-methyl-propanol of the formula III

(b) brominating the compound of formula III with phosphorus tribromide, with triphenylphosphine and bromine in dimethylformamide, or with triphenylphosphine and carbon tetrabromide in methylene chloride to give (S)-(+)-1-bromo-3-chloro-2-methyl-propane of the formula IV

(c) converting the compound of formula IV into (2R)-(+)-1-chloro-2,6-dimethylheptane of the formula V

with isopropyl magnesium bromide in an inert ethereal solvent in the presence of a di-alkali-metal tetrahalocuprate, (d) converting the compound of formula V into (3R)-3,7-dimethyl-octan-1-ol of the formula VI

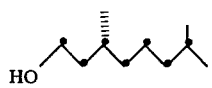 (VI)

by treatment with metallic magnesium in ethereal solution and subsequent introduction of gaseous formaldehyde, (e) brominating the compound of formula VI with phosphorus tribromide, with triphenyl phosphine and bromine in dimethylformamide, or with triphenylphosphine and carbontetrabromide in methylene chloride to give (3R)-1-bromo-3,7-dimethyloctane of the formula VII

 (VII)

(f) converting the compound of formula VII, by treatment with metallic magnesium, into the corresponding Grignard compound, and (g) reacting the Grignard compound with (S)-(+)-1-bromo-3-chloro-2-methylpropane in an ethereal solvent in the presence of a di-alkali-metal tetrahalocuprate to give the compound of formula I.

2. The process of claim 1, wherein the di-alkali-metal tetrahalocuprate is dilithium tetrachlorocuprate.

3. A process for the preparation of (2R,6R)-1-chloro-2,6,10-trimethylundecane of the formula

 (I)

which comprises:

(a) converting (S)-(+)-1-bromo-3-chloro-2-methylpropane of the formula IV

 (IV)

into (2R)-(+)-1-chloro-2,6-dimethylheptane of the formula V

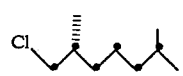 (V)

with isopentyl magnesium bromide in an inert ethereal solvent in the presence of a di-alkali-metal tetrahalocuprate, (b) converting the compound of formula V into (3R)-3,7-dimethyl-octan-1-ol of the formula VI

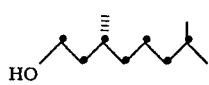 (VI)

by treatment with metallic magnesium in ethereal solution and subsequent introduction of gaseous formaldehyde, (c) brominating the compound of formula VI with phosphorus tribromide, with triphenyl phosphine and bromine in dimethylformamide, or with triphenylphosphine and carbontetrabromide in methylene chloride to give (3R)-1-bromo-3,7-dimethyloctane of the formula VII

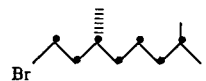 (VII)

(d) converting the compound of formula VII, by treatment with metallic magnesium, into the corresponding Grignard compound, and (e) reacting the Grignard compound with (S)-(+)-1-bromo-3-chloro-2-methyl-propane in an ethereal solvent in the presence of a di-alkali-metal tetrahalocuprate to give the compound of formula I.

4. A process for the preparation of (2R,6R)-1-chloro-2,6,10-trimethylundecane of the formula

 (I)

which comprises:

(a) converting (2R)-(+)-1-chloro-2,6-dimethylheptane of the formula V

 (V)

into (3R)-3,7-dimethyloctan-1-ol of the formula VI

 (VI)

by treatment with metallic magnesium in ethereal solution and subsequent introduction of gaseous formaldehyde, (b) brominating the compound of formula VI with phosphorus tribromide, with triphenyl phosphine and bromine in dimethylformamide, or with triphenylphosphine and carbontetrabromide in methylene chloride to give (3R)-1-bromo-3,7-dimethyloctane of the formula VII

 (VII)

(c) converting the compound of formula VII, by treatment with metallic magnesium, into the corresponding Grignard compound, and (d) reacting the Grignard compound with (S)-(+)-1-bromo-3-chloro-2-methyl-propane in an ethereal solvent in the presence of a di-alkali-metal tetrahalocuprate to give the compound of formula I.

* * * * *